US012797257B2

(12) United States Patent
Jo

(10) Patent No.: US 12,797,257 B2
(45) Date of Patent: Nov. 17, 2026

(54) BRAIN PROTECTION PAD

(71) Applicant: THE CATHOLIC UNIVERSITY OF KOREA INDUSTRY-ACADEMIC COOPERATION FOUNDATION, Seoul (KR)

(72) Inventor: Kwangwook Jo, Bucheon-si (KR)

(73) Assignee: CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 304 days.

(21) Appl. No.: 18/689,744

(22) PCT Filed: Sep. 5, 2022

(86) PCT No.: PCT/KR2022/013271
§ 371 (c)(1),
(2) Date: Mar. 6, 2024

(87) PCT Pub. No.: WO2023/038380
PCT Pub. Date: Mar. 16, 2023

(65) Prior Publication Data

US 2024/0382349 A1 Nov. 21, 2024

(30) Foreign Application Priority Data

Sep. 7, 2021 (KR) ........................ 10-2021-0119378

(51) Int. Cl.
*A61F 13/12* (2006.01)

(52) U.S. Cl.
CPC .................................... *A61F 13/12* (2013.01)

(58) Field of Classification Search
CPC .... A61F 13/12; A61F 2/00; A61F 2/02; A61F 13/00; A61F 2/0063; A61F 13/00063;
(Continued)

(56) References Cited

U.S. PATENT DOCUMENTS

2010/0100022 A1* 4/2010 Greener ............ A61F 13/01038 83/13
2021/0177662 A1* 6/2021 Locke ................ A61F 13/0213

FOREIGN PATENT DOCUMENTS

CN 2732224 10/2005
CN 108272529 7/2018
(Continued)

OTHER PUBLICATIONS

A Self-adhesive Hard Patch and Its Manufacturing Method (Year: 2018).*

*Primary Examiner* — Rebecca E Eisenberg
*Assistant Examiner* — Timothy L Flynn
(74) *Attorney, Agent, or Firm* — NORTON ROSE FULBRIGHT US LLP

(57) ABSTRACT

A brain protection pad is disclosed. A brain protection pad, according to one embodiment of the present invention, comprises an artificial dura mater layer configured to cover the brain exposed to the outside after a craniotomy. The artificial dura mater layer comprises artificial dura mater having a predetermined area so as to cover the brain, and may comprise one or more from among incision portions formed by partially incising the artificial dura mater so as to enable the artificial dura mater to expand in a direction perpendicular to the incision direction, and corrugations formed by folding the artificial dura mater so as to enable the artificial dura mater to expand in an unfolding direction.

9 Claims, 4 Drawing Sheets

(58) Field of Classification Search
CPC .... A61F 2013/00463; A61F 2013/0091; A61F 13/01029; A61F 13/01038; A61F 13/01042
See application file for complete search history.

(56) References Cited

FOREIGN PATENT DOCUMENTS

| | | |
|---|---|---|
| EP | 3085344 | 12/2019 |
| KR | 10-0419563 | 2/2004 |
| KR | 10-1523109 | 5/2015 |
| WO | WO2019/083563 | 5/2019 |

* cited by examiner

BRAIN PROTECTION PAD

CROSS-REFERENCE TO RELATED APPLICATIONS

This application is a national phase application under 35 U.S.C. § 371 of International Application No. PCT/KR2022/013271, filed Sep. 5, 2022, which claims priority to and the benefit of South Korean Application No. 10-2021-0119378, filed Sep. 7, 2021. The contents of the referenced patent applications are incorporated into the present application by reference.

FIELD OF THE DISCLOSURE

The present invention relates to a brain protection pad, and more particularly, to a brain protection pad used to protect a brain instead of dura mater of a patient in a state in which a skull is removed after craniotomy surgery.

DESCRIPTION OF RELATED ART

When the brain significantly swells due to head trauma, cerebral infarction, or cerebral hemorrhage, decompressive craniectomy for removing a portion of a skull to ensure a space in which the brain may swell is performed. In this case, dura mater covering the brain of a patient also needs to expand. To this end, artificial dura mater is sometimes used instead of the dura mater of the patient.

When the artificial dura mater is used, a doctor predicts a degree by which the brain swells and appropriately cuts the artificial dura mater. However, since the artificial dura mater according to the related art rarely expands due to the nature of a material, when the brain swells more than that expected during intensive care unit treatment after surgery, the artificial dura mater according to the related art additionally lacks the ability to response to cerebral edema.

Meanwhile, in the related art, a method of using the dura mater of the patient instead of the artificial dura mater and incising the dura mater in preparation for swelling of the brain is proposed. However, in this method, there is a risk of cerebrospinal fluid leaking to the outside of a body of the patient, and surgical difficulties sometimes occur due to adhesion between the dura mater and a scalp during cranioplasty.

In this situation, there is a need for development of an artificial dura mater that may expand, may prevent drainage of the cerebrospinal fluid, and may not cause adhesion to the scalp.

SUMMARY

The present invention is directed to providing a brain protection pad that may expand when a brain of a patient swells in a state in which the brain protection pad is disposed to protect the brain of the patient of which a skull is removed, and thus provides the ability to respond to the swelling of the brain.

The present invention is also directed to providing a brain protection pad that prevents leakage of a cerebrospinal fluid of the patient in a state in which the brain protection pad is disposed to protect the brain of the patient of which the skull is removed and does not have risk of adhesion to a scalp of the patient.

The present invention is also directed to providing a brain protection pad that supplies an antibiotic agent, a hemostatic agent, and the like together in a state in which the brain protection pad is disposed to protect the brain of the patient of which the skull is removed.

One aspect of the present invention provides a brain protection pad including an artificial dura mater layer that covers brain exposed to an outside after craniotomy surgery, wherein the artificial dura mater layer includes an artificial dura mater body having a predetermined area to cover the brain, and an incision part that allows the artificial dura mater body to expand in a direction perpendicular to an incision direction when the artificial dura mater body is partially incised.

The incision part may be provided as a plurality of incision parts, and the plurality of incision parts may have parallel incision directions.

The artificial dura mater layer may further include a wrinkle part that is formed by folding the artificial dura mater body and allows the artificial dura mater body to expand in an unfolding direction.

The wrinkle part may be formed by folding the artificial dura mater body in the incision direction.

The brain protection pad may further include an absorption layer disposed on one surface of the artificial dura mater layer, wherein the absorption layer may include an absorption body made of an absorption material.

The absorption body may be formed by compressing the absorption material.

The absorption body may be formed by compressing the absorption material in a thickness direction.

The absorption body may be formed by compressing the absorption material in a direction perpendicular to a thickness direction.

The absorption layer may further include an absorption body incision part formed to correspond to the incision part and formed by incising the absorption body such that the absorption body is unfolded along with the incision part when the incision part is unfolded.

The artificial dura mater layer may further include a wrinkle part that is formed by folding the artificial dura mater body and allows the artificial dura mater body to expand in an unfolding direction, and the absorption layer further includes an absorption body wrinkle part formed to correspond to the wrinkle part and formed by folding the absorption body such that the absorption body is unfolded along with the wrinkle part when the wrinkle part is unfolded.

The brain protection pad may further include a drug layer formed by coating one surface of the absorption layer with a drug.

The drug may be an antibiotic agent or a hemostatic agent.

Another aspect of the present invention provides a brain protection pad including an artificial dura mater layer that covers brain exposed to an outside after craniotomy surgery, wherein the artificial dura mater layer includes an artificial dura mater body having a predetermined area to cover the brain, and a wrinkle part that is formed by folding the artificial dura mater body and allows the artificial dura mater body to expand in an unfolding direction.

The brain protection pad may further include an absorption layer disposed on one surface of the artificial dura mater layer, wherein the absorption layer may include an absorption body made of an absorption material.

The absorption layer may further include an absorption body wrinkle part formed to correspond to the wrinkle part and formed by folding the absorption body such that the absorption body is unfolded along with the wrinkle part when the wrinkle part is unfolded.

The brain protection pad may further include a drug layer formed by coating one surface of the absorption layer with a drug.

According to a brain protection pad of the present invention having the above-described configuration, a structure that can expand through one or more of an incision part and a wrinkle part formed on an artificial dura mater layer or the like is provided, making it possible to respond to swelling of a brain.

Further, according to the brain protection pad of the present invention, a cerebrospinal fluid is prevented from being discharged outward through an absorption layer disposed on one surface of the artificial dura mater layer, and adhesion between the artificial dura mater layer in contact with a scalp and the scalp does not occur.

Further, according to the brain protection pad of the present invention, a drug layer including an antibiotic body, a hemostatic agent, or the like is formed on the absorption layer disposed on the one surface of the artificial dura mater layer, and thus the antibiotic body or the hemostatic agent can be supplied to a surgical site.

DETAILED DESCRIPTION OF THE INVENTION

Figure 1:
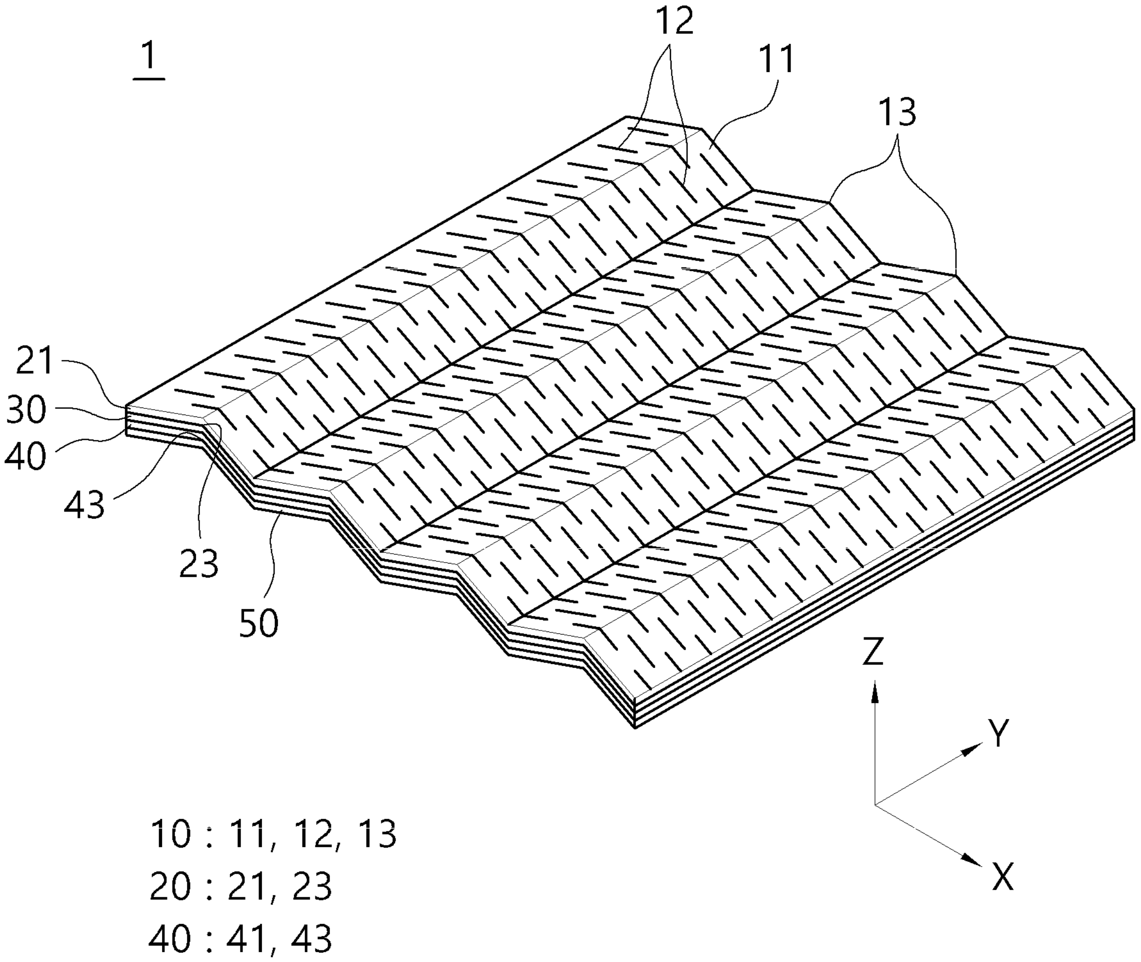
FIG. 1 is a view illustrating a configuration of a brain protection pad according to an embodiment of the present invention.

Hereinafter, embodiments of the present invention will be described in detail with reference to the accompanying drawings so that those skilled in the art to which the present invention pertains may easily implement the present invention. The present invention may be implemented in various different forms and is not limited to the embodiments described herein. In the drawings, parts irrelevant to the description are omitted in order to clearly describe the present invention, and the same reference numerals are assigned to the same or similar components throughout the specification.

It should be understood in the present specification that the terms "include" and "have" are intended to describe that there are features, numbers, steps, operations, components, parts, or combinations thereof that are described in the specification and do not exclude in advance the possibility of the presence or addition of one or more other features, numbers, steps, operations, components, parts, or combinations thereof.

In the present specification, spatially relative terms "front," "rear," "upper," or "lower" may be used to describe a correlation between components illustrated in the drawings. These are relative terms determined on the basis of those illustrated in the drawings, and a positional relationship may be conversely interpreted according to an orientation. Further, a case in which a first component is "connected" to a second component includes a case in which the first component and the second component are indirectly connected to each other as well as a case in which the first component and the second component are directly connected to each other unless otherwise specified.

FIG. 1 is a view illustrating a configuration of a brain protection pad according to an embodiment of the present invention.

A brain protection pad 1 according to the embodiment of the present invention is disposed to protect a brain instead of the dura mater of a patient of which a part or the entirety of a skull is removed. The brain protection pad 1 according to the embodiment of the present invention may expand when the brain of the patient swells and thus provides ability to respond to the swelling of the brain.

Referring to FIG. 1, the brain protection pad 1 according to the embodiment of the present invention may include an artificial dura mater layer 10, a first absorption layer 20, a first drug layer 30, a second absorption layer 40, and a second drug layer 50.

The artificial dura mater layer 10 is provided to cover the brain of the patient, which is exposed to the outside after craniotomy surgery. In the embodiment of the present invention, the artificial dura mater layer 10 may include an artificial dura mater body 11, an incision part 12, and a wrinkle part 13.

The artificial dura mater body 11 has a predetermined area to cover the brain of the patient. The artificial dura mater body 11 may be formed to have a shape and area corresponding to a shape and area of a resection site of the skull. In FIG. 1, the shape of the artificial dura mater body 11 is illustrated as a quadrangular shape, but this is illustrative, and the artificial dura mater body 11 may have a circular shape and may have an atypical shape depending on a shape of the resection site of the skull.

When the artificial dura mater body 11 is partially incised, the incision part 12 allows the artificial dura mater body 11 to expand in a direction perpendicular to an incision direction. The incision part 12 may be provided as a plurality of incision parts 12. In this case, the plurality of incision parts 12 may have incision directions parallel to each other.

Referring to FIG. 1, in the embodiment of the present invention, the plurality of incision parts 12 are spaced apart from each other in a direction parallel to an X axis on an XY plane. Further, the incision parts 12 may be provided in a plurality of rows in a Y-axis direction over the entire area of the artificial dura mater body 11.

Figure 2:
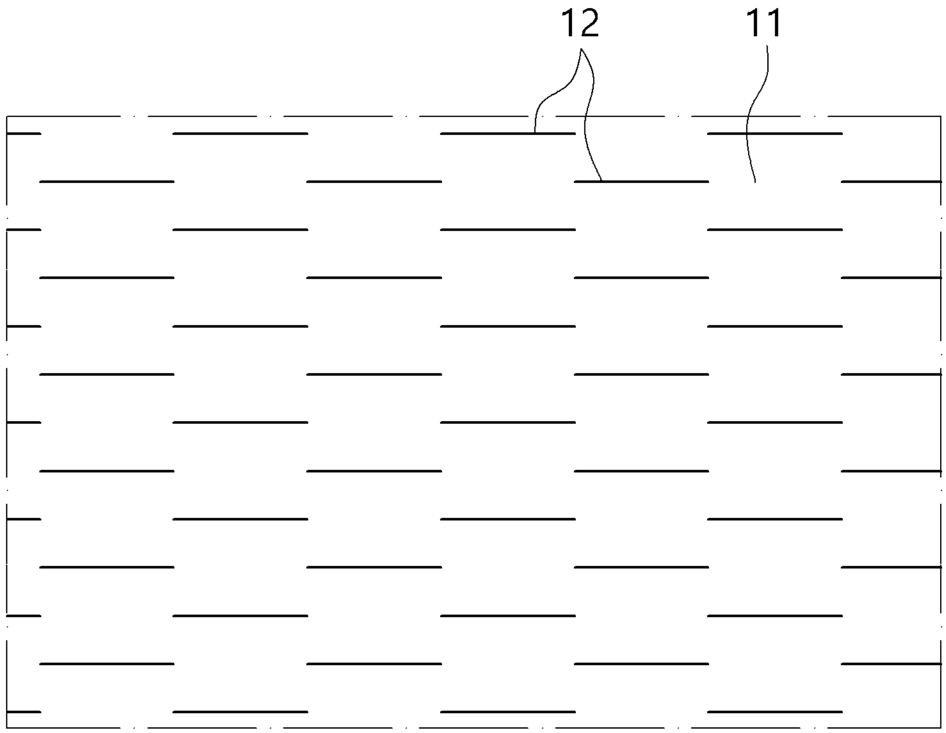
FIG. 2 is an exploded view of one surface of an artificial dura mater layer of the brain protection pad according to the embodiment of the present invention.
Figure 3:
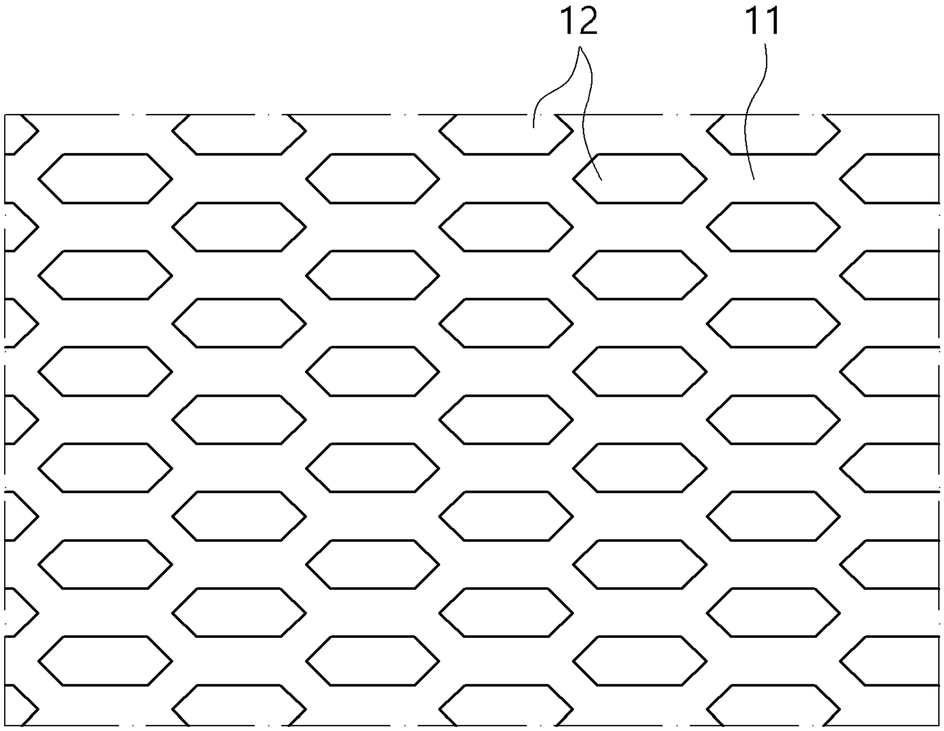
FIG. 3 is a view illustrating an expanded state of an incision part in FIG. 2.

FIG. 2 is an exploded view of one surface of an artificial dura mater layer of the brain protection pad according to the embodiment of the present invention. FIG. 3 is a view illustrating an expanded state of an incision part in FIG. 2.

As illustrated in FIGS. 2 and 3, the incision parts 12 are widened when a force is applied in the direction perpendicular to the incision direction, and accordingly, the artificial dura mater body 11 may expand. When the plurality of incision parts 12 are spaced apart from each other in the direction parallel to the X axis on the XY plane, when a force is applied to the artificial dura mater body 11 in a direction parallel to an Y axis, as the incision parts 12 are widened, the artificial dura mater body 11 may expand.

The wrinkle part 13 is formed by folding the artificial dura mater body 11 and enables the expansion of the artificial dura mater body 11 in an unfolding direction. The wrinkle part 13 may be formed as a plurality of wrinkle parts 13 at regular intervals.

In the embodiment of the present invention, the wrinkle parts 13 may be formed by folding the artificial dura mater body 11 in the incision directions of the incision parts 12. That is, the wrinkle part 13 may be formed such that the artificial dura mater body 11 may be unfolded to expand in the incision direction. In this case, a folding line forming the wrinkle part 13 may be formed in the direction perpendicular to the incision direction of the incision part 12.

As described above, in the embodiment of the present invention, the incision part 12 has an incision direction formed parallel to an X axis and enables the artificial dura mater body 11 to expand in the direction parallel to the Y axis. In addition, when the plurality of wrinkle parts 13 are formed such that the artificial dura mater body 11 may be unfolded in an X-axis direction, the artificial dura mater body 11 may expand even in the direction parallel to the X axis.

Meanwhile, in the embodiment of the present invention, the formation directions of the incision parts 12 and the wrinkle parts 13 are illustrative, and the present invention is not limited by the embodiment. In order to expand the artificial dura mater body 11 in a plurality of directions, the incision part 12 may have two or more different incision directions, and the folding line forming the wrinkle part 13 may be formed in a curved shape.

In this way, the artificial dura mater body 11 of the artificial dura mater layer 10 may expand in the direction parallel to the X axis and also expand in the direction parallel to the Y axis through the incision part 12 and the wrinkle part 13. Therefore, in a state in which the brain protection pad 1 according to the embodiment of the present invention is disposed to cover the brain instead of the brain dura mater of the patient of which a portion of the skull is removed, even when the brain swells, the artificial dura mater layer 10 expands, and thus responses to cerebral edema may be appropriately made.

The first absorption layer 20 is disposed on one surface of the artificial dura mater layer 10. When the first absorption layer 20 is disposed on the one surface of the artificial dura mater layer 10, the other side of the artificial dura mater layer 10 may be disposed in contact with a scalp of the patient. As described above, the artificial dura mater body 11 of the artificial dura mater layer 10 may expand due to the incision part 12 and the wrinkle part 13, and a gap may be formed when the incision part 12 is widened in the direction perpendicular to the incision direction, and blood, cerebrospinal fluid, or the like may flow to the outside of the patient through this gap. The first absorption layer 20 is disposed to solve this problem. That is, the first absorption layer 20 may absorb the blood, the cerebrospinal fluid, or the like of the patient.

The first absorption layer 20 includes a first absorption body 21. For example, the first absorption body 21 may be made of a sponge material. In more detail, the first absorption body 21 may be made of a gelatin sponge material.

Figure 4:
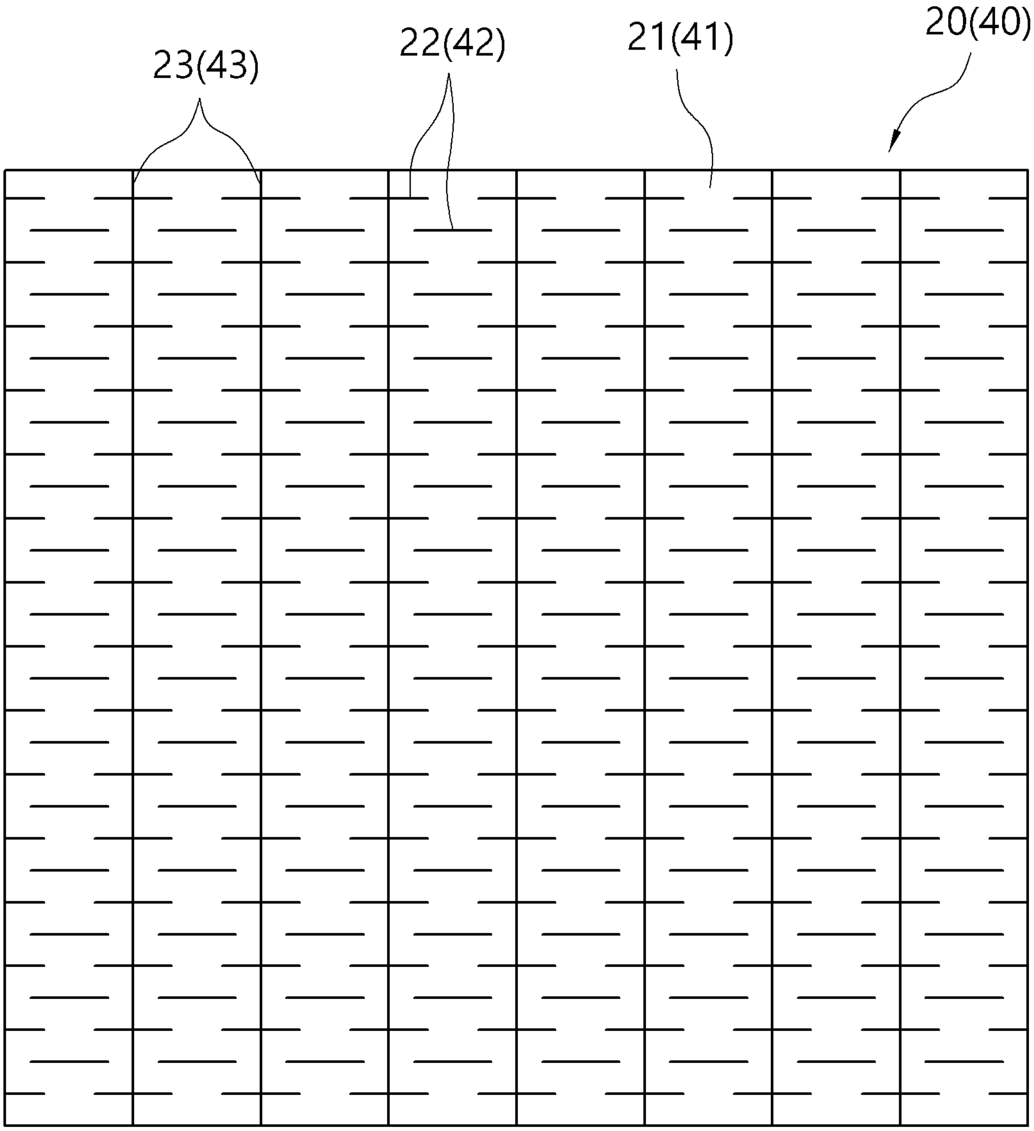
FIG. 4 is a view illustrating one surface of an absorption layer of the brain protection pad according to the embodiment of the present invention.

The first absorption layer 20 may be disposed on the one surface of the artificial dura mater layer 10 and may operate integrally with the artificial dura mater layer 10. To this end, as illustrated in FIG. 4, the first absorption layer 20 may have a first absorption body incision part 22 and a first absorption body wrinkle part 23 corresponding to the incision part 12 and the wrinkle part 13 of the artificial dura mater layer 10.

In other words, the first absorption body incision part 22 is formed to correspond to the incision part 12 and provided such that, when the incision part 12 is unfolded, the first absorption body 21 may be unfolded along with the incision part 12, and the first absorption body wrinkle part 23 is formed to correspond to the wrinkle part 13 and is folded and formed such that, when the wrinkle part 13 is unfolded, the first absorption body 21 may be unfolded along with the wrinkle part 13.

For example, in a state in which the artificial dura mater body 11 and the first absorption body 21 are bonded to each other (which may be a state in which application of the first drug layer 30 may be performed), the artificial dura mater body 11 and the first absorption body 21 are compressed. Thereafter, the incision part 12 and the first absorption body incision part 22 may be formed simultaneously while the artificial dura mater body 11 and the first absorption body 21 are both incised by a punch press or the like, and the wrinkle part 13 and the first absorption body wrinkle part 23 may be formed simultaneously when the artificial dura mater body 11 and the first absorption body 21 are both folded by a press or the like.

In this case, since the first absorption body 21 is made of an absorbent material, even when the first absorption body incision part 22 is widened, the blood, the cerebrospinal fluid or the like passing through the gap formed through the widening are absorbed, and thus the blood, the cerebrospinal fluid or the like fails to reach the artificial dura mater layer 10.

The first drug layer 30 is formed by coating one surface of the first absorption layer 20 with a first drug. In the embodiment of the present invention, the first drug may be an antibiotic agent or a hemostatic agent.

The second absorption layer 40 is disposed on one surface of the first drug layer 30. The second absorption layer 40 is disposed along with the first absorption layer 20 to absorb the blood, the cerebrospinal fluid or the like of the patient.

The second absorption layer 40 includes a second absorption body 41. The second absorption body 41 may be made of the same material as that of the first absorption body 21. For example, the second absorption body 41 may be made of a gelatin sponge material.

The second absorption layer 40 may operate integrally with the artificial dura mater layer 10 and the first absorption layer 20. To this end, as illustrated in FIG. 4, the second absorption layer 40 may be provided with a second absorption body incision part 42 corresponding to the incision part 12 of the artificial dura mater layer 10 and the first absorption body incision part 22 of the first absorption layer 20 and a second absorption body wrinkle part 43 corresponding to the wrinkle part 13 of the artificial dura mater layer 10 and the first absorption body wrinkle part 23 of the first absorption layer 20. That is, the second absorption body incision part 42 is provided such that, when the incision part 12 and the first absorption body incision part 22 are unfolded, the second absorption body 41 may be unfolded along with the first absorption body incision part 22, and the second absorption body wrinkle part 43 is folded and formed such that, when the wrinkle part 13 and the first absorption body wrinkle part 23 are unfolded, the second absorption body 41 may be unfolded along with the wrinkle part 13 and the first absorption body wrinkle part 23.

For example, in a state in which the artificial dura mater body 11, the first absorption body 21, and the second absorption body 41 are bonded to each other (which may be a state in which application of the first drug layer 30 and the second drug layer 50 may be performed), the artificial dura mater body 11, the first absorption body 21, and the second absorption body 41 are all compressed. Thereafter, the incision part 12, the first absorption body incision part 22, and the second absorption body incision part 42 may be formed simultaneously while the artificial dura mater body 11, the first absorption body 21, and the second absorption body 41 are all incised by a punch press or the like, and the wrinkle part 13, the first absorption body wrinkle part 23, and the second absorption body wrinkle part 43 may be formed simultaneously when the artificial dura mater body 11, the first absorption body 21, and the second absorption body 41 are all folded by a press or the like.

For example, in a state in which the artificial dura mater body 11, the first absorption body 21, and the second absorption body 41 are bonded to each other (which may be a state in which application of the first drug layer 30 and the second drug layer 50 may be performed), a total thickness thereof may be in a range of 1 cm to 1.5 cm, and a thickness of the brain protection pad 1 compressed through a roller or the like may be in a range of 2 mm to 8 mm.

In this case, since the second absorption body 41 is made of an absorbent material, even when the second absorption body incision part 42 is widened, the blood, the cerebrospinal fluid or the like passing through the gap formed through the widening is absorbed, and the blood, the cerebrospinal fluid or the like fails to reach the artificial dura mater layer 10.

Further, in the embodiment of the present invention, since the second absorption body 41 and the first absorption body 21 are both stacked and arranged, even when the blood, the cerebrospinal fluid or the like passes through the second absorption body incision part 42 of the second absorption body 41, the passing of the blood, the cerebrospinal fluid or the like may be blocked by the first drug layer 30 or the blood, the cerebrospinal fluid or the like may be absorbed by the first absorption body 21, and thus the blood, the cerebrospinal fluid or the like may be prevented from overflowing outward.

The second drug layer 50 is formed by coating one surface of the second absorption layer 40 with a second drug. In the embodiment of the present invention, the second drug may be an antibiotic agent or a hemostatic agent. When the first drug is an antibiotic agent, the second drug is preferably a hemostatic agent, and when the first drug is a hemostatic agent, the second drug is preferably an antibiotic agent.

Meanwhile, in the embodiment of the present invention, the first absorption body 21 and the second absorption body 41 may be made by compressing an absorbent material. The first absorption body 21 and the second absorption body 41 may be made by compressing the absorbent material in a thickness direction (a direction parallel to a Z axis in FIG. 1) or may be made by compressing the absorbent material in a direction perpendicular to the thickness direction (e.g., a direction parallel to the X axis or the Y axis in FIG. 1).

For example, the first absorption body 21 may be made through compression in the direction perpendicular to the thickness direction, and the second absorption body 41 may be made through compression in the thickness direction. When the first absorption body 21 and the second absorption body 41 are arranged in a compressed state, when the first absorption body 21 and the second absorption body 41 absorb the blood, the cerebrospinal fluid or the like, the first absorption body 21 and the second absorption body 41 expand. In this way, when a compression direction of the first absorption body 21 and a compression direction of the second absorption body 41 are different from each other, the direction of expansion due to the absorption may be diversified.

Further, in the embodiment of the present invention, the first absorption body 21 and the second absorption body 41 may be absorbed and disappear into a body of the patient after three to six months. In this case, since the first drug layer 30 and the second drug layer 50 disappear as the first drug and the second drug are absorbed into the body, only the artificial dura mater layer 10 may finally serve as dura mater and remain in the body.

The brain protection pad 1 according to the embodiment of the present invention may be used to cover the entire brain while fixed to a bone in a state in which the entire skull is removed. In this case, a surgery time may be shortened. Thereafter, suturing may be performed through cranioplasty.

Figure 5:
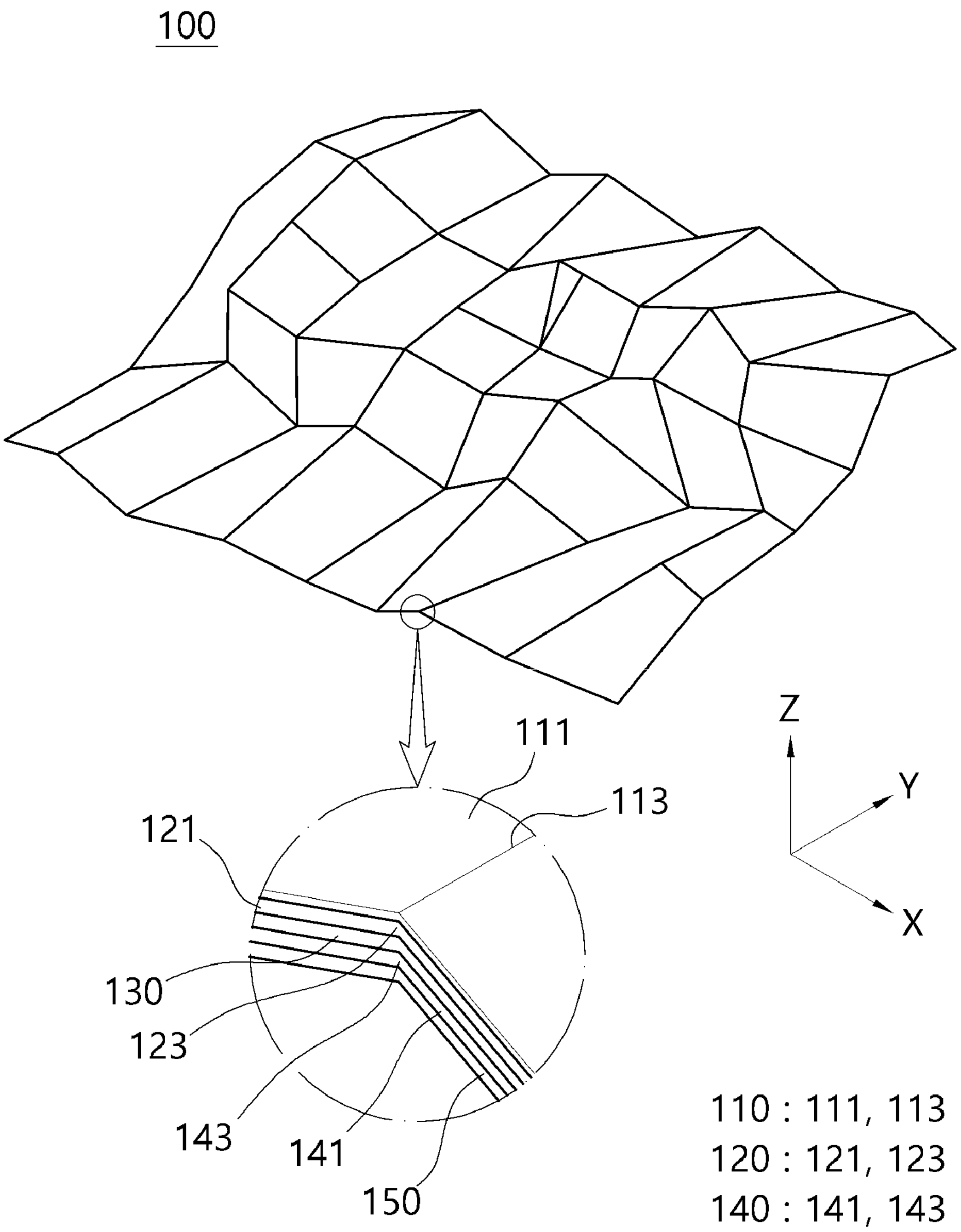
FIG. 5 is a view illustrating a configuration of a brain protection pad according to another embodiment of the present invention.

FIG. 5 is a view illustrating a configuration of a brain protection pad according to another embodiment of the present invention.

Like the brain protection pad 1 according to another embodiment of the present invention, a brain protection pad 100 according to another embodiment of the present invention is disposed to protect the brain instead of the dura mater of the patient of which a portion or the entirety of the skull is removed. The brain protection pad 100 according to another embodiment of the present invention may expand when the brain of the patient swells, thereby providing ability to respond to the swelling of the brain.

Referring to FIG. 5, the brain protection pad 100 according to another embodiment of the present invention may include an artificial dura mater layer 110, a first absorption layer 120, a first drug layer 130, a second absorption layer 140, and a second drug layer 150.

The artificial dura mater layer 110 is provided to cover the brain of the patient, which is exposed to the outside after craniotomy surgery. In another embodiment of the present invention, the artificial dura mater layer 110 may include an artificial dura mater body 111 and a wrinkle part 113. As described in relation to the embodiment of the present invention, the artificial dura mater body 111 may have a predetermined area to cover the brain of the patient and may be formed to have a shape and area corresponding to a shape and area of the resection site of the skull.

The wrinkle part 113 is formed by folding the artificial dura mater body 111 and enables the expansion of the artificial dura mater body 111 in an unfolding direction. That is, the wrinkle part 113 may be formed such that the artificial dura mater body 111 may be unfolded to expand. In FIG. 5, the wrinkle part 113 is formed to have a random shape so that the wrinkle part 113 may expand in all directions. In this case, the wrinkle part 113 may include a portion formed in a curved shape. However, this is illustrative, and the wrinkle part 113 may be regularly formed in an X direction or a Y direction.

The first absorption layer 120 is disposed on one surface of the artificial dura mater layer 110. When the first absorption layer 120 is disposed on the one surface of the artificial dura mater layer 110, the other side of the artificial dura mater layer 110 may be disposed in contact with the scalp of the patient. The first absorption layer 120 includes a first absorption body 121. For example, the first absorption body 121 may be made of a sponge material. In more detail, the first absorption body 121 may be made of a gelatin sponge material.

The first absorption layer 120 may be disposed on the one surface of the artificial dura mater layer 110 and may operate integrally with the artificial dura mater layer 110. To this end, as illustrated in FIG. 5, the first absorption layer 120 may be provided with a first absorption body wrinkle part 123 corresponding to the wrinkle part 113 of the artificial dura mater layer 110. In other words, the first absorption body wrinkle part 123 is formed to correspond to the wrinkle part 113 and is folded and formed so that, when the wrinkle part 113 is unfolded, the first absorption body 121 is unfolded along with the wrinkle part 113.

The first drug layer 130 is formed by coating one surface of the first absorption layer 120 with the first drug. In another embodiment of the present invention, the first drug may be an antibiotic agent or a hemostatic agent.

The second absorption layer 140 is disposed on one surface of the first drug layer 130. The second absorption layer 140 is disposed along with the first absorption layer 120 to absorb the blood, the cerebrospinal fluid or the like of the patient.

The second absorption layer 140 includes a second absorption body 141. The second absorption body 141 may be made of the same material as that of the first absorption body 121. For example, the second absorption body 141 may be made of a gelatin sponge material.

The second absorption layer 140 may operate integrally with the artificial dura mater layer 110 and the first absorption layer 120. To this end, as illustrated in FIG. 5, the second absorption layer 140 may be provided with a second absorption body wrinkle part 143 corresponding to the wrinkle part 113 of the artificial dura mater layer 110 and the first absorption body wrinkle part 123 of the first absorption layer 120. That is, the second absorption body wrinkle part 143 is folded and formed such that, when the wrinkle part 113 and the first absorption body wrinkle part 123 are unfolded, the second absorption body 41 may be unfolded along with the wrinkle part 113 and the first absorption body wrinkle part 123.

The second drug layer 150 is formed by coating one surface of the second absorption layer 140 with the second drug. In another embodiment of the present invention, the second drug may be an antibiotic agent or a hemostatic agent. When the first drug is an antibiotic agent, the second drug is preferably a hemostatic agent, and when the first drug is a hemostatic agent, the second drug is preferably an antibiotic agent.

In addition, among the contents described in relation to the embodiment of the present invention, the remaining contents except for those related to the incision part may be directly applied to the brain protection pad 100 according to another embodiment of the present invention.

Although embodiments of the present invention have been described, the spirit of the present invention is not limited to the embodiments presented in the present specification. Those skilled in the art who understand the spirit of the present invention can easily propose other embodiments by adding, changing, deleting, adding, or the like of components within the same scope of the spirit. However, these other embodiments also belong to the scope of the spirit of the present invention.

The invention claimed is:

1. A brain protection pad comprising an artificial dura mater layer configured to cover brain exposed to an outside after craniotomy surgery, wherein the artificial dura mater layer includes:

an artificial dura mater body having a predetermined area to cover the brain; and an incision part configured to allow the artificial dura mater body to expand in a direction perpendicular to an incision direction when the artificial dura mater body is partially incised, wherein the incision part is provided as a plurality of incision parts, and the plurality of incision parts have parallel incision directions, wherein the artificial dura mater layer further includes a wrinkle part formed by folding the artificial dura mater body and configured to allow the artificial dura mater body to expand in an unfolding direction, and wherein the wrinkle part is formed as a plurality of wrinkle parts at regular intervals along the incision direction of the incision parts, and folding lines forming the plurality of wrinkle parts extend in a direction perpendicular to the incision direction of the incision parts.

2. The brain protection pad of claim 1, further comprising an absorption layer disposed on one surface of the artificial dura mater layer, wherein the absorption layer includes an absorption body made of an absorption material.

3. The brain protection pad of claim 2, wherein the absorption body is formed by compressing the absorption material.

4. The brain protection pad of claim 3, wherein the absorption body is formed by compressing the absorption material in a thickness direction.

5. The brain protection pad of claim 3, wherein the absorption body is formed by compressing the absorption material in a direction perpendicular to a thickness direction.

6. The brain protection pad of claim 2, wherein the absorption layer further includes an absorption body incision part formed to correspond to the incision part and formed by incising the absorption body such that the absorption body is unfolded along with the incision part when the incision part is unfolded.

7. The brain protection pad of claim 2, wherein the artificial dura mater layer further includes a wrinkle part formed by folding the artificial dura mater body and configured to allow the artificial dura mater body to expand in an unfolding direction, and the absorption layer further includes an absorption body wrinkle part formed to correspond to the wrinkle part and formed by folding the absorption body such that the absorption body is unfolded along with the wrinkle part when the wrinkle part is unfolded.

8. The brain protection pad of claim 2, further comprising a drug layer formed by coating one surface of the absorption layer with a drug.

9. The brain protection pad of claim 8, wherein the drug is an antibiotic agent or a hemostatic agent.

* * * * *